United States Patent
Naumann et al.

(10) Patent No.: US 9,084,993 B2
(45) Date of Patent: Jul. 21, 2015

(54) PIPETTING APPARATUS WITH A PIPETTING HEAD COMPRISING A MULTIPLICITY OF PIPETTING CHANNELS DISPOSED IN AN ARRANGEMENT PATTERN

(71) Applicant: CyBio AG, Jena (DE)

(72) Inventors: Uwe Naumann, Jena (DE); Torsten Schoeppe, Jena (DE); Heiko Oehme, Jena (DE); Thomas Moore, Drackendorf (DE)

(73) Assignee: ANALYTIK JENA AG, Jena (DE)

( * ) Notice: Subject to any disclaimer, the term of this patent is extended or adjusted under 35 U.S.C. 154(b) by 366 days.

(21) Appl. No.: 13/622,493

(22) Filed: Sep. 19, 2012

(65) Prior Publication Data

US 2013/0068041 A1    Mar. 21, 2013

(30) Foreign Application Priority Data

Sep. 20, 2011    (DE) .......................... 10 2011 053 808

(51) Int. Cl.
  *B01L 3/02*    (2006.01)
  *G01N 35/10*    (2006.01)

(52) U.S. Cl.
  CPC ............. *B01L 3/0217* (2013.01); *B01L 3/0275* (2013.01); *G01N 35/1074* (2013.01); *B01L 2200/023* (2013.01)

(58) Field of Classification Search
  USPC ........................................................ 73/864.01
  See application file for complete search history.

(56) References Cited

U.S. PATENT DOCUMENTS

| | | | |
|---|---|---|---|
| 6,244,119 B1 | 6/2001 | Theran | |
| 6,589,483 B1 | 7/2003 | Maeda | |
| 6,841,130 B2 | 1/2005 | Lehtinen et al. | |
| 6,982,063 B2* | 1/2006 | Hamel et al. | 422/511 |
| 7,335,337 B1* | 2/2008 | Smith | 422/513 |
| 7,713,481 B2 | 5/2010 | Naumann | |
| 7,897,111 B2 | 3/2011 | Naumann | |
| 2005/0220676 A1* | 10/2005 | Tran | 422/100 |
| 2007/0048188 A1 | 3/2007 | Bigus | |
| 2009/0233816 A1 | 9/2009 | Aoki et al. | |
| 2010/0196212 A1* | 8/2010 | Reed et al. | 422/100 |
| 2012/0258026 A1 | 10/2012 | Naumann | |

FOREIGN PATENT DOCUMENTS

| | | |
|---|---|---|
| DE | 260571 A1 | 9/1988 |
| DE | 4104831 A1 | 10/1992 |
| DE | 19734599 A1 | 2/1999 |
| DE | 10344700 A1 | 4/2005 |
| DE | 202004007120 U1 | 9/2005 |

(Continued)

*Primary Examiner* — Laura Martin
*Assistant Examiner* — Herbert K Roberts
(74) *Attorney, Agent, or Firm* — Leydig, Voit & Mayer, Ltd.

(57) ABSTRACT

A pipetting apparatus includes a pipetting head with a plurality of pipetting channels disposed in an arrangement pattern. Each pipetting channel includes a plunger and a cylinder. The plurality of pipetting channels includes at least two groups of pipetting channels with different diameters including a group of larger pipetting channels and a group of smaller pipetting channels. Each of the at least two groups of pipetting channels is disposed in an arrangement pattern in the pipetting head. Larger pipette tips communicate with the group of larger pipetting channels or smaller pipette tips communicate with the group of smaller pipetting channels.

9 Claims, 10 Drawing Sheets

(56) References Cited

FOREIGN PATENT DOCUMENTS

| DE | 60013983 | T2 | 10/2005 |
| DE | 202007000904 | U1 | 4/2007 |
| DE | 202008013533 | U1 | 1/2009 |
| DE | 202011000837 | U1 | 7/2011 |
| EP | 1070540 | A2 | 1/2001 |
| EP | 1214977 | B1 | 10/2009 |
| WO | WO 2011110141 | A1 | 9/2011 |

\* cited by examiner

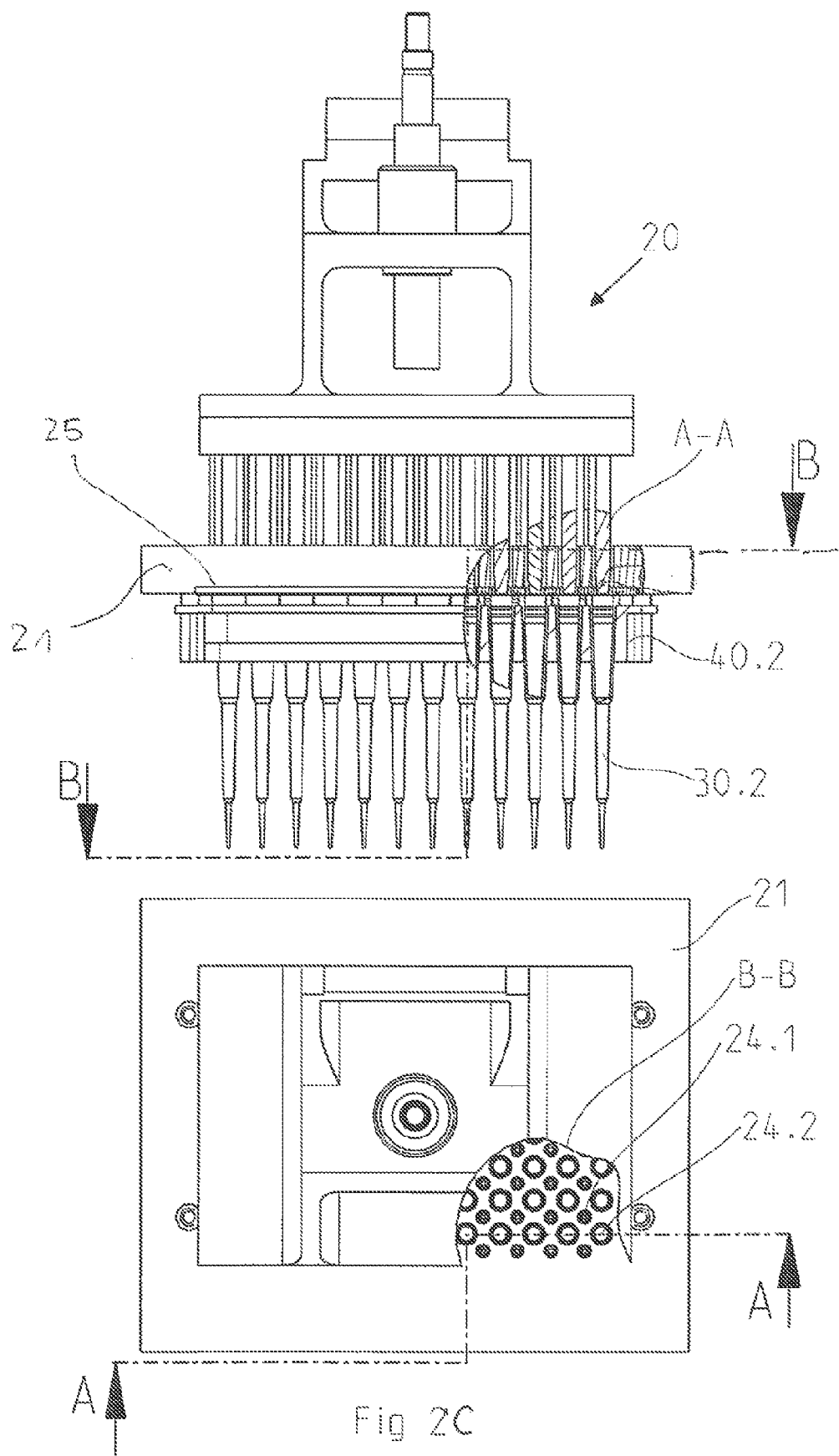

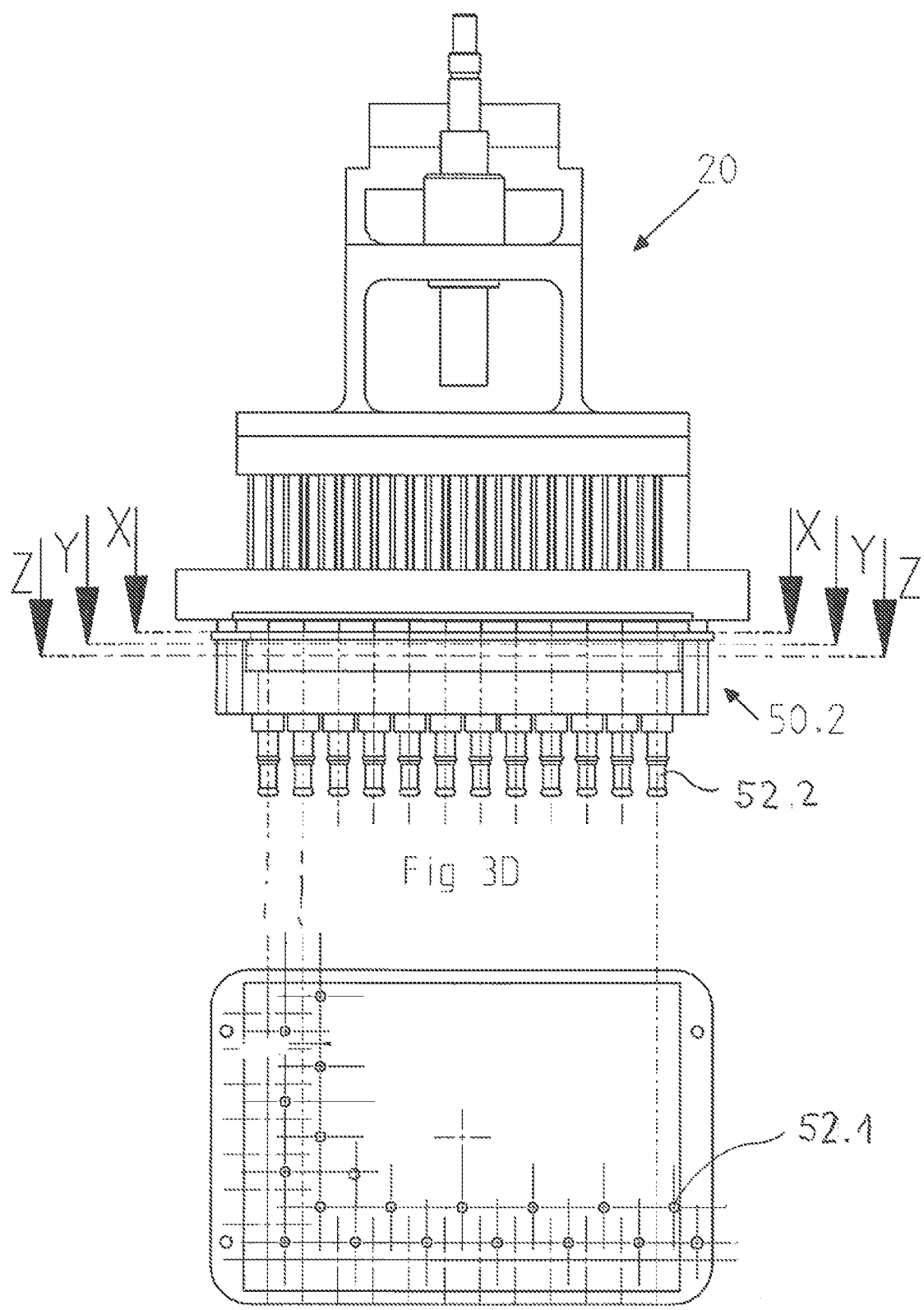

PIPETTING APPARATUS WITH A PIPETTING HEAD COMPRISING A MULTIPLICITY OF PIPETTING CHANNELS DISPOSED IN AN ARRANGEMENT PATTERN

CROSS REFERENCE TO RELATED APPLICATIONS

This application claims priority to German Patent Application No. DE 10 2011 053 808.9, filed Sep. 20, 2011, which is hereby incorporated by reference herein in its entirety.

BACKGROUND

The invention relates to a pipetting apparatus with a pipetting head comprising a one-dimensional or two-dimensional arrangement of pipetting channels and an arrangement of releasable pipette tips in communication with the pipetting channels. Each pipetting channel is formed by a plunger and a cylinder, wherein the plungers are guided in the cylinders and are sealed with respect to the cylinders. The cylinder may be provided as a bushing consisting of an elastic material and tightly enclosing the plunger, thereby already achieving a sealing effect. In order to enable a matrix-shaped arrangement of pipetting channels, said bushings are suitably arranged with respect to each other in through bores, e.g. in a rigid plate. The cylinders may also be formed by the through bores of one or more plates arranged above one another. The sealing of the plunger is then usually achieved by additional sealing elements, such as spring-supported rings, sealing sleeves and/or O rings or X rings, respectively.

The cylinders, and thus the pipetting channels, are mounted in a predetermined mutual arrangement pattern in a base plate of the pipetting head. The arrangement pattern usually corresponds to a grid, formed by the intersections of rows and columns disposed perpendicular to each other, with the same grid distance between the axes of the pipetting channels, said grid distance being downwardly limited by a smallest useful diameter of the cylinders and a minimum wall thickness between the cylinders.

The pipette tips are arranged on or around the cylinders in a similar arrangement as the pipetting channels, usually releasable via a seal.

This type of pipetting head and this type of pipetting apparatus are generically known from EP 1,214,977 B1.

Due to the operating principle of the pipetting channels, such pipetting apparatuses are also referred to as air displacement pipettors, air displacement dispensers or air-cushion pipettes.

If it is desired to express the multiplicity rather than the operating principle of the pipetting channels, such pipetting apparatuses are referred to, for example, as simultaneous pipettors, multi-well pipettors, multi-channel dispensers, multi-channel dosage devices, multi-channel pipettes or multi-channel dispensers.

In this type of apparatus, the arrangement pattern, and consequently the spacing and number of the pipetting channels, are usually based on what is called the microtiter plate grid. Typical microtiter plate grids have grid spacings between the axes of the pipetting channels of 9 mm, 4.5 mm, or 2.25 mm and a number of (1), 4, 8, 12, 16, (24, 32, 48) 96, 384 and, in exceptional cases, even 1536 pipetting channels.

Many apparatuses differ further in the way the pipette tips are fastened to and sealed with respect to the pipetting channels.

On the one hand, some devices have complete analogy to hand pipettes, e.g. as described in DE 4 104 831 A1, comprising what is known as receiving cones or receiving shafts (cylindrical or other shape) on which the pipette tips are fitted and sometimes also sealed with what is called an O ring. A device of this type is described in DD 260 571.

On the other hand, there are devices, such as that described in DE 20 2008 013 533 U for example, wherein the sealing surfaces on the end faces of the pipette tips suspended in magazines are jointly pressed against a perforated, plane, elastic sealing mat. This connecting principle between the pipetting channels and the pipette tips has been embodied by the applicant's CyBi-well product family for many years. Pipetting apparatuses with various means for receiving magazines are described, for example, in DE 20 2007 000 904 U and DE 20 2011 000 837 (still unpublished).

The invention described below is applicable to all of the above-mentioned pipetting apparatuses which have exchangeable pipette tips (which is what they are called here) or similarly usable tubes (canulas) or the like. It does not matter whether the pipette tips are so-called disposable articles (injection-molded plastic disposables) or metal, glass or ceramics articles, or reusable plastic articles. Nor does it matter whether the pipetting apparatus is an electro-mechanical or a mechanical pipetting apparatus.

In the practical application of hand pipettes, their users are faced with the everyday situation of selecting the appropriate pipette for the application at hand, usually on the basis of the volume range to be handled. Many laboratories are equipped with pipette stands holding a range of various hand pipettes.

The more channels such a hand pipette has, the more dexterity will be required of its user, and pipettes with 96 or more channels have been properly usable only as standalone devices.

Standalone devices are much more expensive than hand pipettes and also require a lot of space on the lab counter.

Thus, laboratory users are very often faced with the question which pipetting apparatus with what pipetting volume range is the right one. This consideration often leads to the purchase of several apparatuses and, consequently, big investments.

One solution consists in systems with so-called exchangeable heads, i.e. the user buys one basic device and exchangeable pipetting heads.

These devices are optimal for many users because they allow quick and easy re-fitting. One example of such devices is the "CyBi-well vario" system offered by the applicant and described, inter alia, in DE 20 2007 000 904 U. However, due to the required mechanical precision and reliability, such devices are structurally complex, heavy and still expensive.

Moreover, especially when it comes to automatically processable pipetting protocols, it is tedious and unproductive to have to interrupt liquid-handling processes in order to exchange the pipetting heads for the transfer of other volumes.

Several suggestions have been made on how to expand the volume range which can be handled by a pipetting apparatus, i.e. the range between a minimum and a maximum pipettable volume per pipette tip, without exchanging the pipetting head.

DE 41 04 831 A1 describes a pipetting channel (called dosage device in this case) for manual and motor-driven single- and multiple-channel dosage devices, said channel differing from conventional pipetting channels in that it comprises an inner plunger guided within an outer plunger, allowing a large volume to be received in the pipette tip via the plunger stroke of the outer plunger and a small volume to be received in a much more sensitive manner via the plunger stroke of the inner plunger. This solution, known for almost 20 years, requires very complex technology and is still not widely used in practice today.

DE 600 13 983 T2 describes a special pipette tip in which more than only one pipetting channel terminates. The tip may enclose different numbers of pipetting channels or their openings, respectively, depending on the shape and dimensions of the tip collar (called the crown in this case). Such pipette tips have the disadvantage that they must be specially designed, which in turn requires specially shaped and dimensioned seals as well as specially adapted magazines by which the pipette tips can be fitted on the pipetting head.

EP 1,214,977 B1 shows a multi-channel-pipetting apparatus comprising a number of pipetting channels which are connected to pipette tips by an adapter plate such that each pipette tip has at least two pipetting channels assigned to it. Similar to the arrangement pattern of the pipetting channels, the adapter plate comprises a pattern of channel inlets of thinner channels on one side, which are combined in groups inside the adapter to form thicker channels whose outlets are determined by the arrangement pattern of the pipette tips, which corresponds to a microtiter plate grid. This has the particular disadvantage that a pipetting apparatus comprising, for example, 96 pipetting channels, in which the adapter allows to combine, e.g. four pipetting channels each in one pipette tip, can only be pipetted via 24 pipette tips. In other words, the greater the volume to be handled per pipette tip, the smaller will be the number of the pipettable volumes. The enlargement of the pipettable volume is effected, as in accordance with DE 600 13 983 T2, in a linear manner, as a function of the number of pipetting channels connected to each other; in the example just explained, this corresponds merely to a four-fold increase when connecting 4 pipetting channels.

SUMMARY

In an embodiment, the present invention provides a pipetting apparatus including a pipetting head with a plurality of pipetting channels disposed in an arrangement pattern. Each pipetting channel includes a plunger and a cylinder. The plurality of pipetting channels includes at least two groups of pipetting channels with different diameters including a group of larger pipetting channels and a group of smaller pipetting channels. Each of the at least two groups of pipetting channels is disposed in an arrangement pattern in the pipetting head. Larger pipette tips communicate with the group of larger pipetting channels or smaller pipette tips communicate with the group of smaller pipetting channels.

BRIEF DESCRIPTION OF THE DRAWINGS

The invention will be explained below with reference to exemplary embodiments and to the attached drawings, in which:

FIG. 2C shows another embodiment of a pipetting apparatus with a pipetting head according to FIG. 2A and a second magazine 40.2, equipped with larger pipette tips 30.2;

FIGS. 3D-3H show another embodiment of a pipetting apparatus with a pipetting head according to FIG. 3A and of a second adapter plate 50.2, designed for larger pipette tips 30.2.

DETAILED DESCRIPTION

Figure 1:
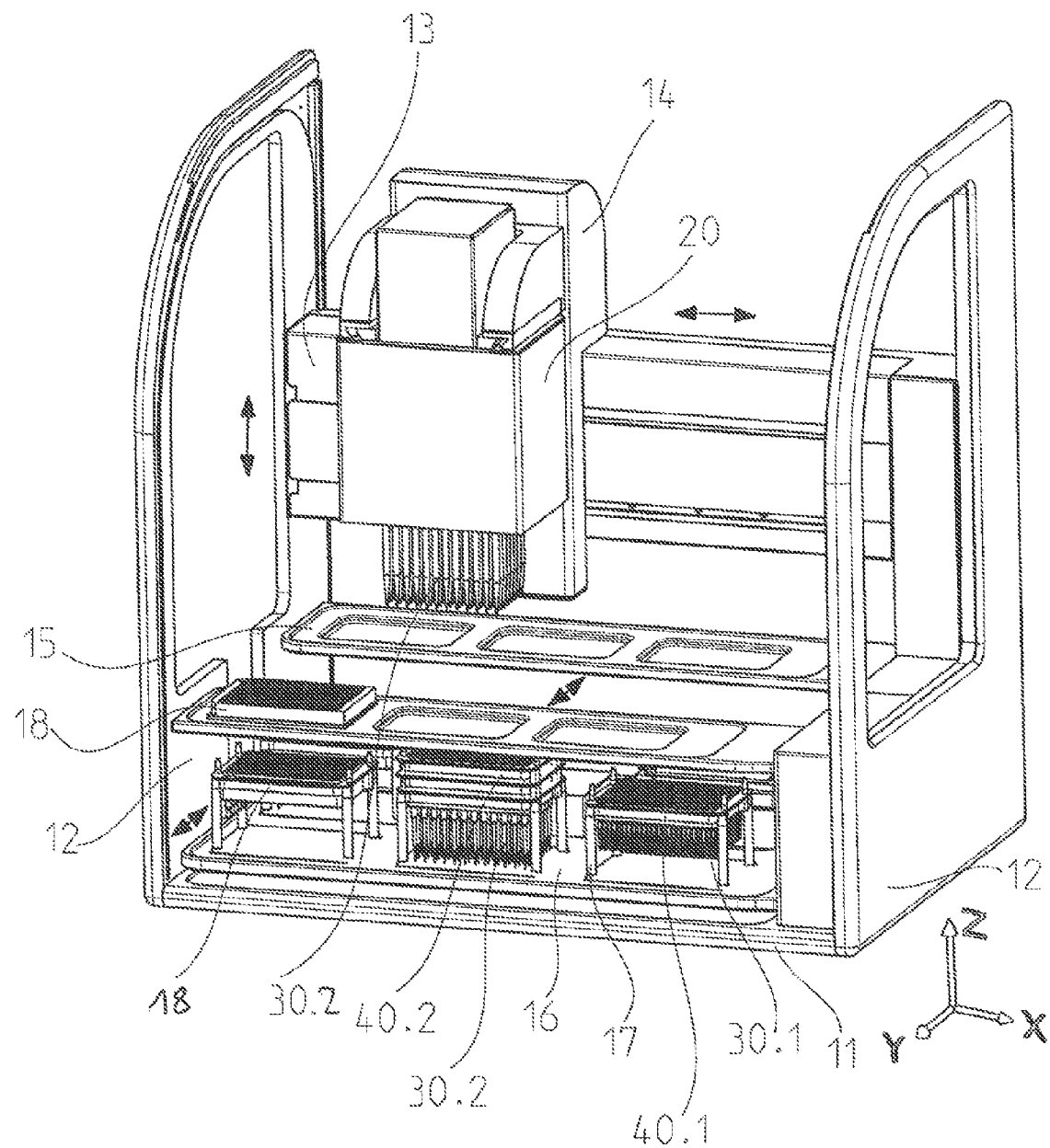
FIG. 1 shows a multi-channel pipetting system comprising a multi-channel pipetting apparatus and ancillary equipment.

In an embodiment, the present invention provides a pipetting apparatus with a pipetting head which allows the volume potentially receivable and dispensable by the individual pipette tips to be adapted to the requirements at hand over a larger volume range.

In an embodiment, the pipetting apparatus is provided with a pipetting head comprising a multiplicity of pipetting channels disposed in an arrangement pattern, wherein each of said pipetting channels is formed by a plunger and a cylinder and wherein at least two groups of pipetting channels having different diameters are present. Each of said groups of pipetting channels is disposed in an arrangement pattern in the pipetting head. The pipetting apparatus comprises larger pipette tips communicating with the larger pipetting channels, or smaller pipette tips communicating with the smaller pipetting channels. The groups of pipetting channels are each disposed in an arrangement pattern in the pipetting head. The pipetting apparatus comprises larger pipette tips communicating with the larger pipetting channels, or smaller pipette tips communicating with the smaller pipetting channels. Both arrangement patterns may be equal or different and arranged with a mutual offset or next to each other.

Advantageously, exactly two groups of pipetting channels are present, namely a group of larger pipetting channels with a greater diameter and a group of smaller pipetting channels with a smaller diameter, both arrangement patterns respectively corresponding to an identical grid of a standardized microtiter plate and being arranged with a mutual offset.

In order to allow the larger pipetting channels to be made much larger, the group of smaller pipetting channels may comprise an arrangement pattern which corresponds only to part of a grid of a standardized microtiter plate, thus leaving a large area next to it for the arrangement pattern of the larger pipetting channels.

Advantageously, the arrangement pattern of the group of smaller pipetting channels corresponds to an arrangement of marginal wells of the microtiter plate in the shape of an L.

The arrangement pattern of the group of larger pipetting channels may then be advantageously formed by arranging the pipetting channels in at least two rows and columns with a mutual offset.

The sealing of the pipette tips with respect to the pipetting channels is advantageously achieved by a sealing plate contacting the pipetting head and having a pattern of holes which comprises both arrangement patterns.

Advantageously, an at least partially filled first magazine for smaller pipette tips or an at least partially filled second magazine for larger pipette tips is in force-fitting contact with the pipetting head in the pipetting apparatus, said magazines differing in the diameter of the holes as well as the position of the hole patterns with respect to the outer edges of the magazines.

Advantageously, the pipetting apparatus comprises an adapter plate comprising a number of channels that corresponds to the number of smaller pipetting channels or to the number of larger pipetting channels, wherein the channel inlets are arranged in the same pattern as the arrangement pattern of the respective opposite pipetting channels and a pattern formed by the channel outlets corresponds to a grid or part of a grid of a standardized microtiter plate, which allows, in particular, arrangement patterns of a group of large pipetting channels to be adapted to the grid of standardized microtiter plates, even with very small grid spacings.

FIG. 1 schematically shows a multi-channel pipetting system in which a pipetting apparatus according to an embodiment of the invention can be used in an advantageous manner.

The entire multi-channel pipetting system is accommodated in a housing, of which only the base plate 11 and two side walls 12 are depicted here. Between the side walls 12, directly in front of a rear wall and parallel to the base plate 11, a first guide rail 13 is mounted, on which a second guide rail 14 is installed, which is displaceable in the direction of x and on which a pipetting head 20 is mounted, which is in turn displaceable in the direction of z. The pipetting head 20 shown here, which constitutes subject matter of the invention and which will be explained in more detail with reference to the attached drawings, is equipped with second pipette tips 30.2 as an example and is located in an upper position on the second guide rail 14.

Below the second guide rail 14, parallel to the base plate 11, two upper transport vehicles 15 with rectangular openings are mounted in an upper plane and one lower transport vehicle 16 with a closed placement area is mounted in a lower plane, all of said vehicles being displaceable in the direction of y. For instance, microtiter plates 18, adapter plates 50.1, 50.2 as well as magazines 40.1, 40.2—either equipped with pipette tips 30.1, 30.2 or empty—can stand on the lower transport vehicle 16 individually or in a stacked manner and are shown here as placed in three locations in holders 17 provided for this purpose. From the observer's point of view, the drawing shows a microtiter plate 18 in the left-hand placement location, second magazines 40.2 equipped with larger pipette tips 30.2 in the central placement location, and first magazines 40.1 equipped with smaller pipette tips 30.1 in the right-hand placement location, each placed in their holders 17.

A microtiter plate 18 is placed on one of the upper transport vehicles 15, above one of the rectangular openings.

Due to the translational degrees of freedom of the entire multi-pipetting system, the pipetting head 20 and the placement locations, or the rectangular openings, can be advanced with respect to each other such that the pipette tips, depending on whether they are held—suspended indirectly in a magazine via an adapter plate or suspended directly in a magazine—on the pipetting head 20 by a force-fit connection via a sealing plate or several sealing rings, or whether the pipette tips are mounted in a form-fit and force-fit manner on cones provided for this purpose on the pipetting head 20, can be received by the pipetting head 20 and the pipetting head 20 can be moved over microtiter plates 18 placed on the upper transport vehicles 15 so as to carry out a pipetting operation.

The equipping of the transport vehicles 15, 16 can be carried out by handling robots, which engage openings provided for this purpose in the side walls, or manually.

In such a multi-channel pipetting system, the benefits of a pipetting head 20 according to an embodiment of the invention show to advantage because the pipetting head 20 can be combined quickly and automatically with different magazines 40.1, 40.2 for pipette tips 30.1, 30.2 of different diameters as well as, optionally, with an adapter plate 50.1, 50.2 to form differently designed pipetting apparatuses so as to be optimized for different volume ranges.

Figure 2A:
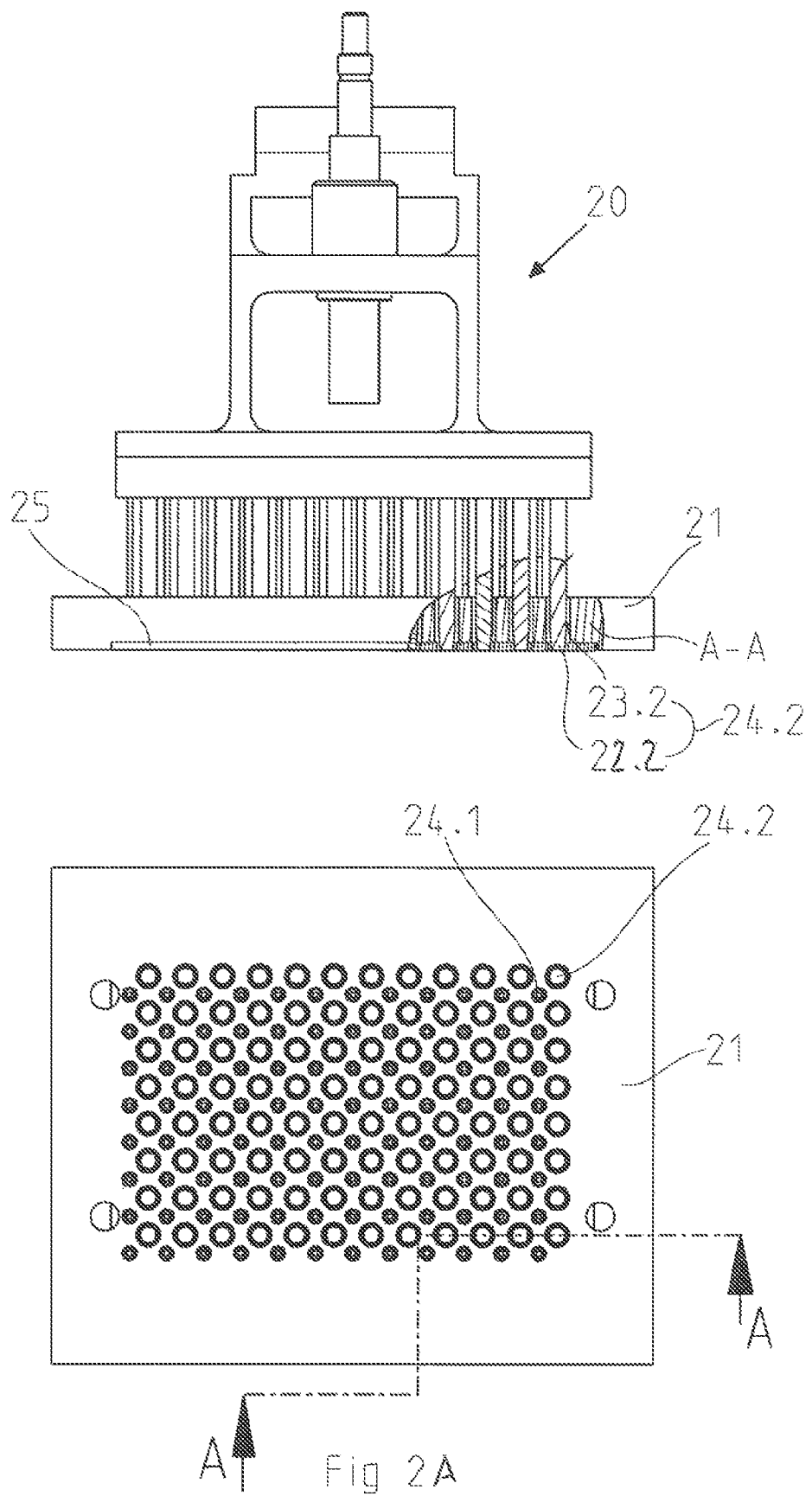
FIG. 2A shows a pipetting head according to an embodiment.
Figure 2B:
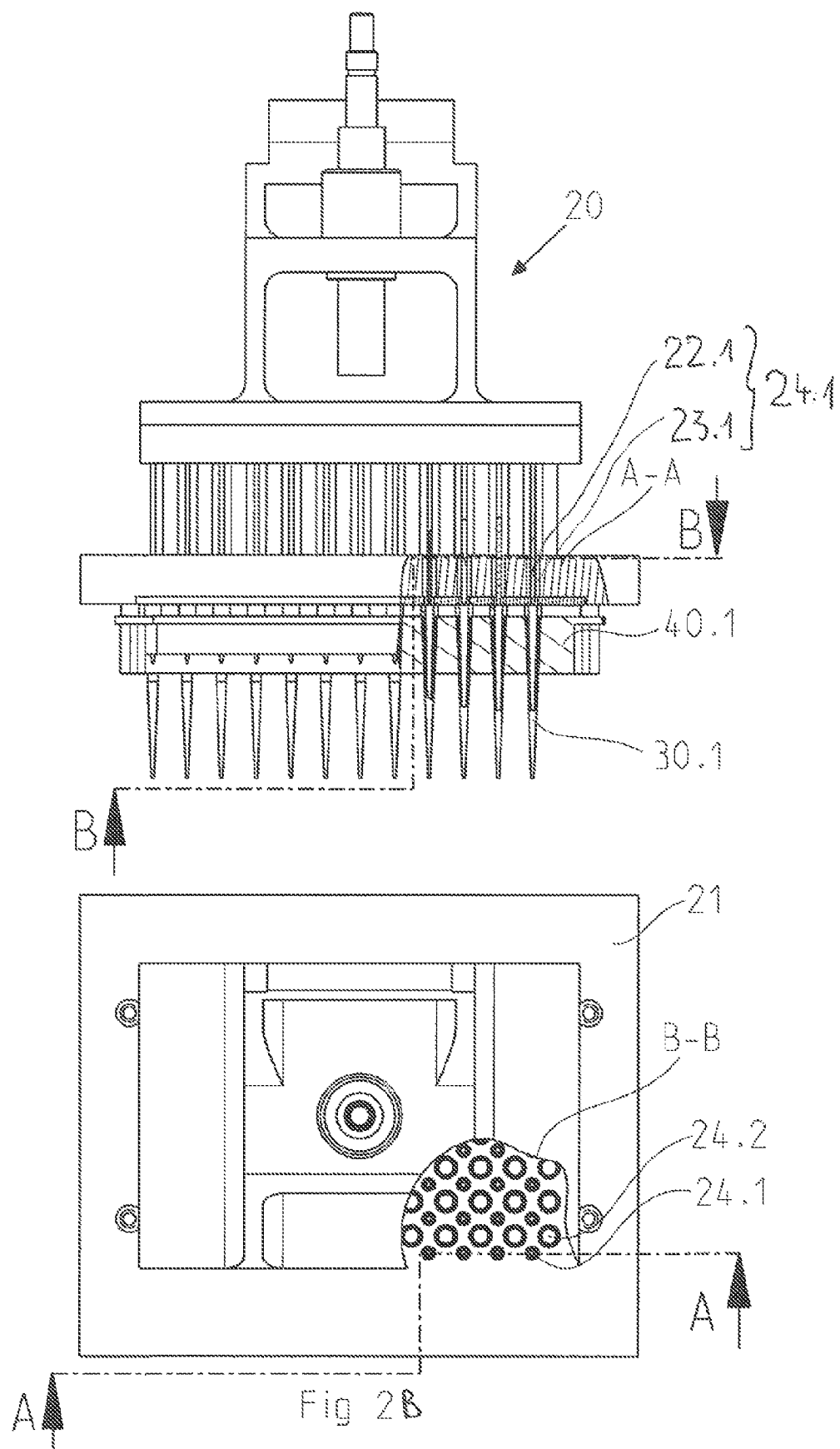
FIG. 2B shows an embodiment of a pipetting apparatus with a pipetting head according to FIG. 2A and a first magazine 40.1, equipped with smaller pipette tips 30.1.

FIGS. 2A to 2C show a pipetting head 20 according to an embodiment as well as two embodiments of a pipetting apparatus comprising such a pipetting head 20 and a magazine 40.1, 40.2, equipped with pipette tips 30.1, 30.2.

In contrast to the prior art, according to which pipetting heads comprise a two-dimensional, regular arrangement of pipetting channels, i.e. same-diameter pipetting channels arranged in a grid, pipetting heads 20 according to an embodiment of the invention have in common that they comprise at least two groups of pipetting channels 24.1, 24.2 in different sizes, i.e. with different diameters. They are disposed in an arrangement pattern which does not necessarily correspond to a grid.

As explained at the beginning, a grid is understood to be an arrangement pattern formed by the points of intersection of mutually perpendicular rows and columns with an identical grid spacing between the points of intersection. If pipetting channels are disposed in an arrangement pattern which corresponds to a grid, the axes of the pipetting channels pass through these points of intersection. If the grid of the pipetting channels is adapted to that of a standardized microtiter plate, then the distances between the axes will be selected to correspond to the centre-to-centre distances between the wells of standardized microtiter plates. The grids will be considered as identical if the pipetting channels and wells are assigned to each other one-on-one, i.e. each well is assigned to a particular pipetting channel and each pipetting channel is assigned to a particular well. If there is a well for each pipetting channel, but not a pipetting channel for each well, then the grid of the pipetting channels corresponds to part of the grid of the microtiter plate.

As explained below, the arrangement patterns of the at least two groups of different-sized pipetting channels can correspond to a grid or part of a grid of a standardized microtiter plate or differ from it.

According to the embodiment of FIGS. 2A-2C, two groups of pipetting channels 24.1, 24.2 are present in a pipetting head 20, namely one group of larger pipetting channels 24.2 and one group of smaller pipetting channels 24.1. The larger pipetting channels 24.2 comprise plungers 22.2 with a larger diameter and consequently cylinders 23.2 with a larger diameter as compared to the smaller pipetting channels 24.1. Apart from this difference that at least two groups of different-sized pipetting channels 24.1, 24.2 are present, a pipetting head 20 according to the invention may be of the same as conventional constructions.

The greater the difference in diameter between the pipetting channels 24.1, 24.2 of the two groups, the greater will be the volume range—which is a function of the square of half of the diameter—to which a pipetting head 20 embodied therewith and a pipetting apparatus equipped therewith can be adapted.

According to the embodiment of FIGS. 2A-2C, each of the two groups of pipetting channels 24.1, 24.2 is disposed in an arrangement pattern corresponding to a grid. Both grids correspond exactly to the grid of a standardized 96-well microtiter plate 18, i.e. there are 8×12 pipetting channels 24.1 and 8×12 pipetting channels 24.2, with a 9 mm spacing between them. As shown in the lower illustration of FIG. 2A, showing the pipetting head 20 from below without the sealing plate 25, the smaller pipetting channels 24.1 are each arranged in the middle between four adjacent, larger pipetting channels 24.2. Accordingly, both groups are arranged with a mutual offset in identical grids. The smaller pipetting channels 24.1 advantageously have a minimal diameter of, for example, 1.5 mm, whereas the larger pipetting channels 24.2, limited by the grid spacing and the interposition of the smaller pipetting channels 24.1, may have a diameter of e.g. 4.5 mm. The volume which the larger pipetting channels 24.2 can theoretically receive is thus about 10 times that of the smaller pipetting channels 24.1.

Just as in conventional constructions, each of the total of 192 pipetting channels 24.1, 24.2 consists of a plunger 22.1, 22.2 guided in a cylinder 23.1, 23.2, which cylinders 23.1, 23.2 are formed in a carrier plate 21 of the pipetting head 20. The plungers 22.1, 22.2 are moved in a conventional manner via a joint screw drive. Below the carrier plate 21, a sealing plate 25 with 192 holes is mounted, with the pattern of the holes corresponding to the superposition of both grids with the respective diameters. A contact pressure device provided on the pipetting head 20 can be connected to two different magazines 40.1, 40.2—depending on whether pipetting is to be effected via the smaller or the larger pipetting channels 24.1, 24.2—said magazines being equipped either with smaller pipette tips 30.1, i.e. pipette tips with a smaller receiving volume, in particular less than/equal to 60 ml, or with larger pipette tips 30.2, i.e. pipette tips with a larger receiving volume, in particular greater than/equal to 200 ml. The magazines 40.1, 40.2 differ accordingly in the diameter of the holes and in the position of the hole pattern, which also corresponds to the grid of a 96-well microtiter plate 18, with respect to the outer edges of the magazine 40.1, 40.2.

In order to allow the contact pressure device to be designed in a conventional manner for magazines 40.1, 40.2 that have the same outer dimensions, either both magazines 40.1, 40.2 can be embodied such that their grid centers are offset in the opposite direction with respect to the centre of the magazine 40.1, 40.2, or that the grid centre of one of the magazines 40.1, 40.2 is in the centre of the magazine 40.1, 40.2 and only the grid centre of the other magazine 40.1, 40.2 is offset.

If, as shown in FIG. 2B, the magazine 40.1 with the smaller pipette tips 30.1 is mounted on the pipetting head 20, then the smaller pipette tips 30.1 are connected to the smaller pipetting channels 24.1. Analogously, as shown in FIG. 2C, the larger pipette tips 30.2 are connected to the larger pipetting channels 24.2. This allows handling of a volume range of at least from 100 nl to 2504 µl.

The connection of the pipette tips 30.1, 30.2 need not be effected in the described manner by a force-fit connection to a sealing plate 25, but may also be effected, in particular for a lower number of pipetting channels 24.1, 24.2, as known as an alternative connection in the prior art, by forming cones on the cylinders 23.1, 23.2, on which cones the pipette tips can be fitted directly, or indirectly via an O ring.

FIGS. 3A to 3H show a pipetting head 20 according to another embodiment as well as exemplary embodiments of a pipetting apparatus comprising such a pipetting head 20 and an adapter 50.1, 50.2, equipped with pipette tips 30.1, 30.2.

Similar to the embodiment described above, the pipetting head 20 comprises two groups of pipetting channels 24.1, 24.2, namely one group of larger pipetting channels 24.2 and one group of smaller pipetting channels 24.1. In contrast to the above-described exemplary embodiment, these two groups constitute different arrangement patterns formed next to each other.

The arrangement pattern of the group of smaller pipetting channels 24.1 corresponds to part of a grid of a standardized microtiter plate 18, in this case a 384-well microtiter plate with a grid spacing of 2.25 mm. The arrangement pattern of the group of larger pipetting channels 24.2 corresponds neither to a grid nor to part of a grid of a standardized microtiter plate 18.

To allow the larger pipetting channels 24.2 to be provided with an even larger diameter than that to which they are limited by a grid spacing of the microtiter plates 18 when they are arranged next to each other, the pipetting channels 24.2 are arranged in two rows and columns with a mutual offset. The larger pipetting channels 24.2 might also be arranged in the carrier plate 21, distributed in a manner differing from the arrangement pattern shown, e.g. on circular arcs or even in a seemingly arbitrary manner. As shown below, what matters is that non-intersecting channels are guided within an adapter plate 50.2, which channels the respective arrangement pattern adapts to part of a grid of a standardized microtiter plate.

Figure 3A:
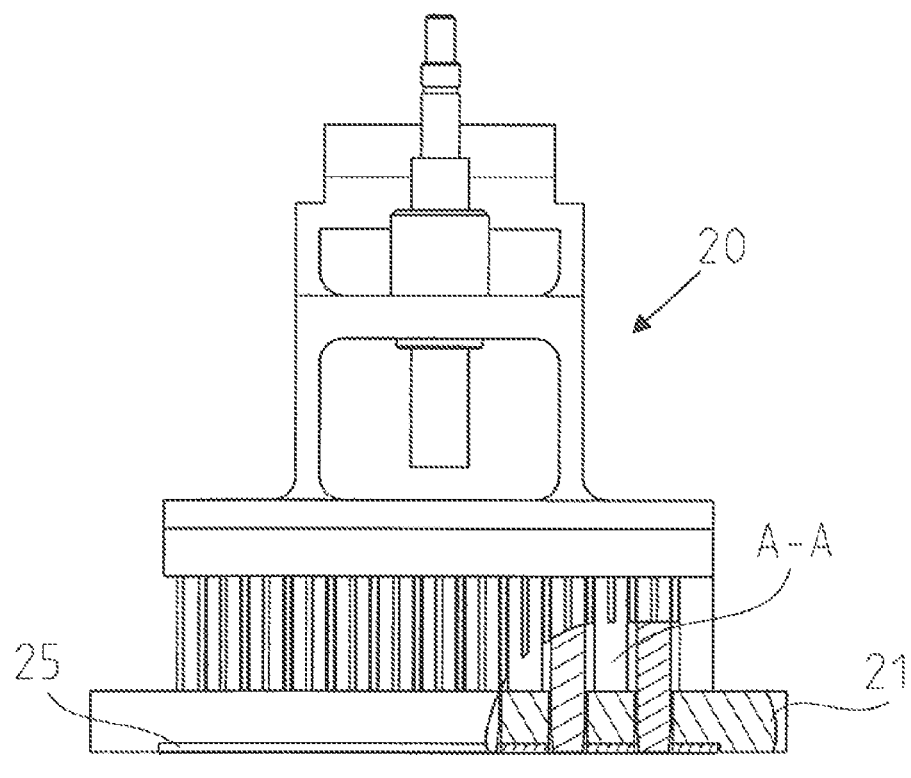
FIG. 3A shows a pipetting head according to another embodiment.
Figure 3A:
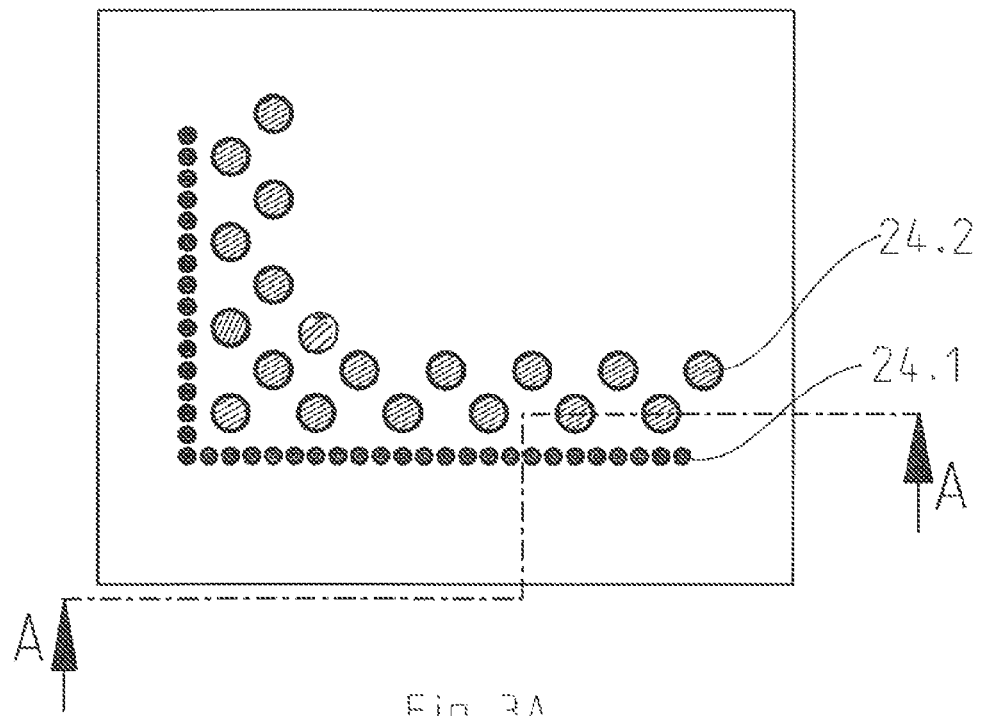

The described combination of arrangement patterns, shown in FIG. 3A, is advantageous, in particular, if the diameter of the smaller pipetting channels 24.1 is very small and the diameter of the larger pipetting channels 24.2 is very large. This allows handling of a volume range of at least from 100 nl to 1000 µl.

According to this embodiment of a pipetting head 20, 39 of the smaller pipetting channels 24.1 are arranged with a spacing (pitch) of 4.5 mm in the shape of an L, i.e. in one line and one column, such that their arrangement corresponds to that of the marginal wells of a 384-well microtiter plate. Therefore, the arrangement pattern of this group corresponds to part of the grid of a 384-well microtiter plate 18. As previously described, 19 of the larger pipetting channels 24.2 are arranged within the area delineated by the two legs of the "L", as already described. As usual, all of these pipetting channels 24.1, 24.2 have plane elastomer seals on their end faces, which seals—as explained with reference to the first exemplary embodiments for a pipetting head 20—are in turn quite simply provided as a sealing plate 25 made from an elastomer, e.g. silicone rubber.

A pipetting apparatus with such a pipetting head 20 may be completed in different ways by equipping it with pipette tips 30.1, 30.2.

As in the embodiment of FIGS. 2A-2C for a pipetting head 20, a first magazine 40.1, partly filled with 39 smaller pipette tips 30.1, or a second magazine 40.2, partly filled with 19 larger pipette tips 30.2, could be pressed against and fixed to the pipetting head 20 in an arrangement similar to that of the pipetting channels 24.1, 24.2.

However, such a solution might not make sense for the group of the larger pipetting channels 24.2, because there are neither matching microtiter plates 18 nor similar containers for the arrangement pattern of this group, nor would the use of newly created, suitable microtiter plates 18 or similar containers provide any advantage; on the contrary, it would even require more space.

This is where another idea of the invention comes in useful, according to which the pipette tips 30.1, 30.2 are not fixed directly to the pipetting head 20, but indirectly, via an adapter plate 50.1, 50.2 which adapts the arrangement pattern of the groups of pipetting channels 24.1, 24.2 to a grid or part of a grid of a standardized microtiter plate 18. This allows arrangement patterns of groups of large pipetting channels 24.2 to be adapted to the grids of standardized microtiter plates 18, even with very small grid spacings.

Figure 3B:
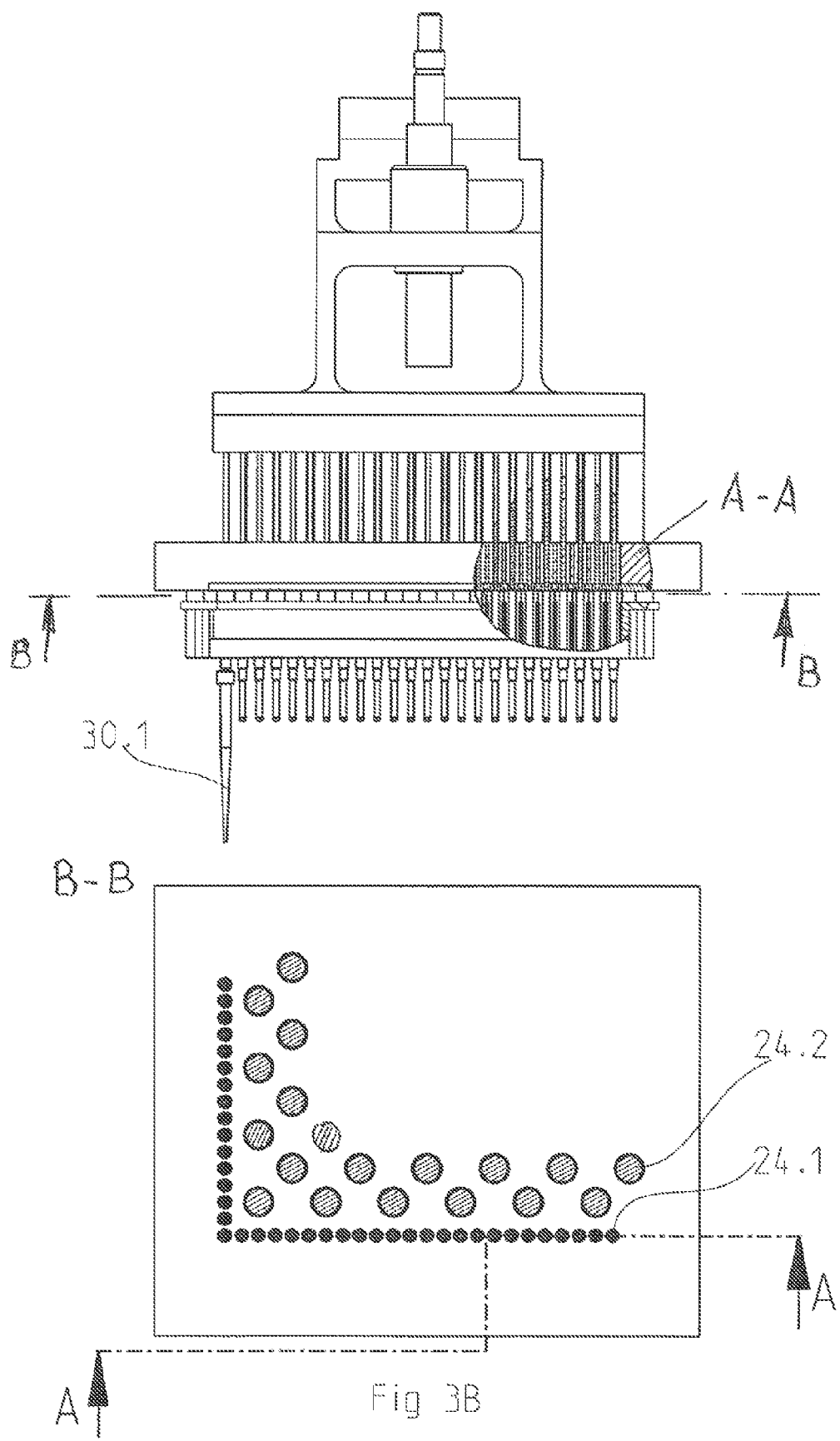
FIGS. 3B-3C show an embodiment of a pipetting apparatus with a pipetting head according to FIG. 3A and of a first adapter plate 50.1, equipped with smaller pipette tips 30.1.

For a pipetting head 20 according to the embodiment of FIGS. 3A-3H, a pipetting apparatus equipped with it will be described below, wherein the two groups of pipetting channels 24.1, 24.2 are connected to pipette tips 30.1, 30.2 via an adapter plate 50.1, 50.2, as shown in FIG. 3B.

Such an adapter plate 50.1, 50.2 basically consists of a number of channels guided through the adapter plate 50.1, 50.2, equal to the number of pipetting channels 24.1, 24.2 of the group of pipetting channels to be adapted. The channel inlets have an arrangement pattern identical with that of the group of pipetting channels 24.1, 24.2 to be adapted, whereas the channel outlets comprise a grid which corresponds to part of the grid of a standardized microtiter plate 18.

The adapter plate 50.1, 50.2 may be sealed both with respect to the pipetting channels 24.1, 24.2 and the pipette tips 30.1, 30.2 by end face-contacting sealing rings, a sealing plate, or, as shown here, by sealing shafts 51.1, 51.2 formed on the adapter plate.

Sealing with respect to the pipette tips 30.1, 30.2 may be effected, as also known, by pushing the pipette tips 30.1, 30.2 indirectly or directly onto cones formed at the channel outlets.

Figure 3C:
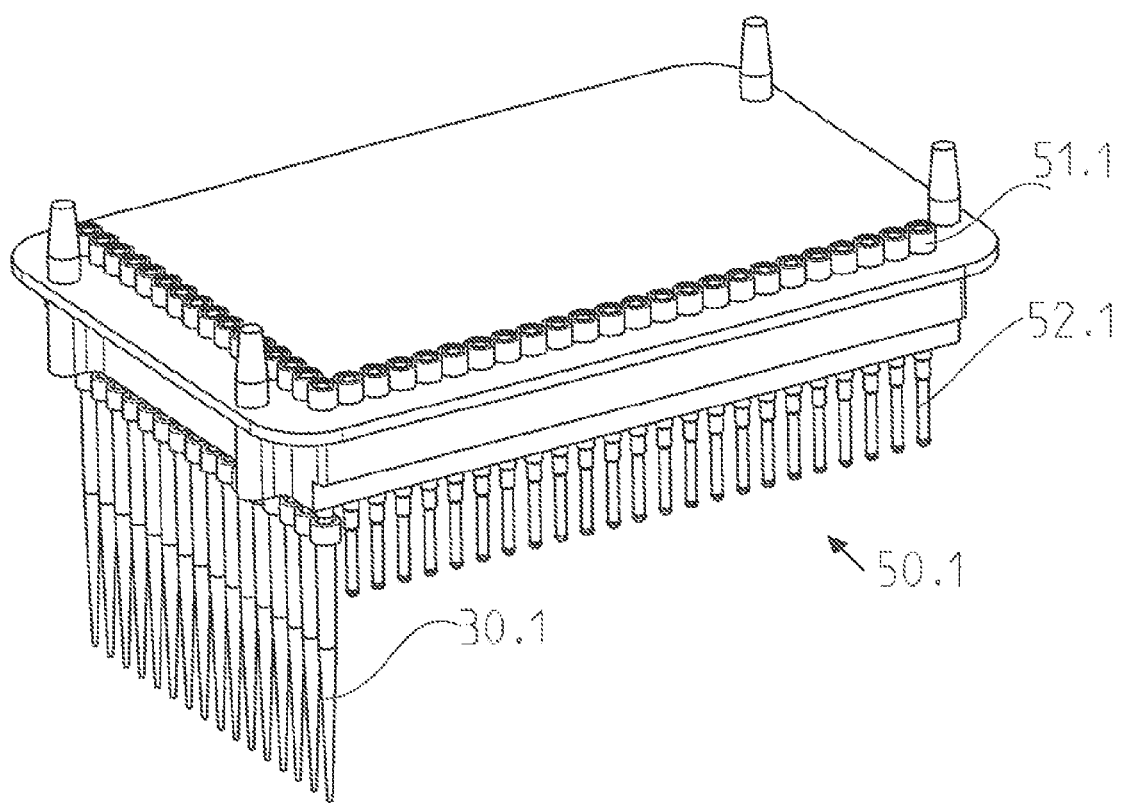
Figure 3C:
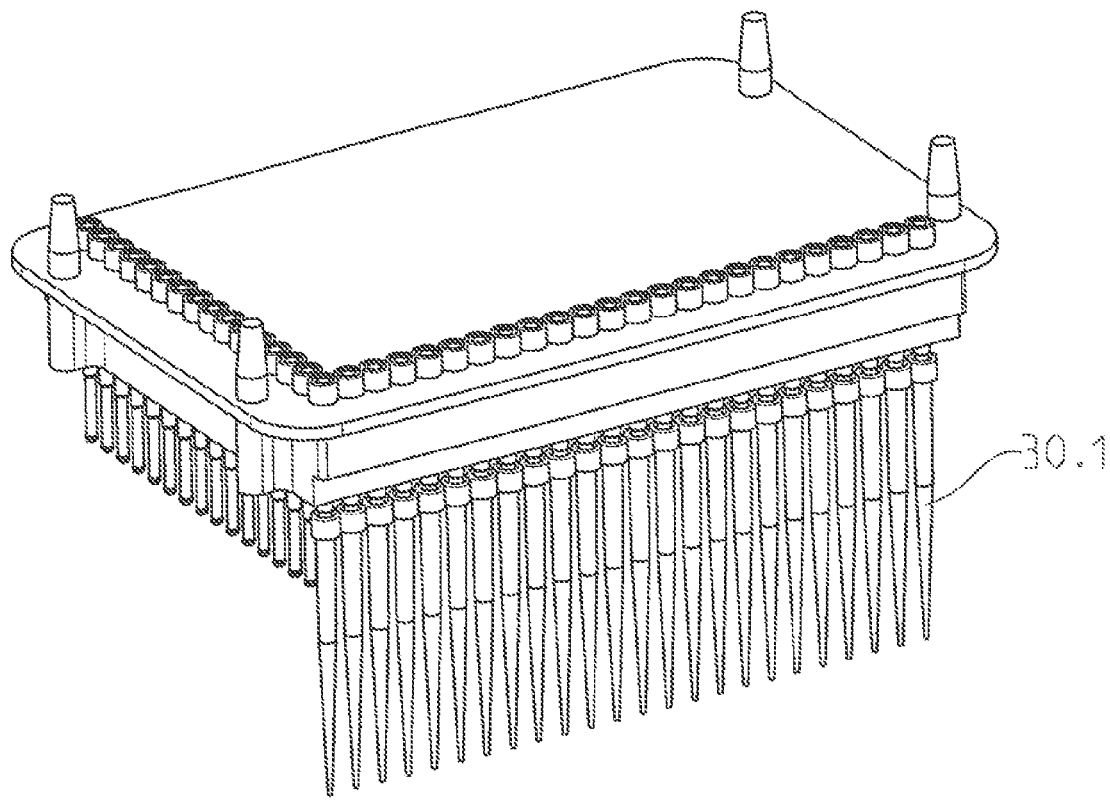

In the present example, a first adapter plate 50.1 for the group of smaller pipetting channels 24.1, shown in FIG. 3C, comprises exactly 39 channel inlets forming an "L"-shaped hole pattern and, accordingly, 39 first receiving shafts 52.1.

The first adapter plate 50.1 is sealed with the 39 channel inlets against the sealing plate 25. Depending on the particular application, e.g. 16 smaller pipette tips 30.1 can now be fitted on the first receiving shafts 52.1, so that the pipetting apparatus can perform pipetting/dispensing operations (incl. mixing, serial dilution, direct dilution, etc.) in a longitudinal/row direction (landscape format). If the first adapter plate 50.1 is equipped with only 24 smaller pipette tips 30.1 in the column direction, operations can be carried out analogously, but perpendicular to the former direction. Of course, it is also possible to employ a lower number of smaller pipette tips 30.1, e.g. every second, fourth or even only one smaller pipette tip 30.1. This makes it possible to generate different pipetting patterns or to address individual wells, called single wells.

The use of a first adapter plate 50.1 in combination with the use of the smaller pipette tips 30.1 also serves to allow operation of the pipetting apparatus in the direction of z with respect to a microtiter plate 18, regardless of which of the pipette tips 30.1, 30.2 are being used.

A second adapter plate 50.2 for the group of larger pipetting channels 24.2, shown in FIGS. 3D and 3E, comprises channels whose channel inlets are disposed in accordance with the arrangement pattern of the group of larger pipetting channels 24.2 and whose outlets also comprise an "L"-shaped arrangement of second receiving shafts 52.2, this time with double the grid spacing of a 96-well microtiter plate 18.

In contrast to the channels of the above-described first adapter plate 50.1, the channel inlets and outlets of a second adapter plate 50.2 for the group of larger pipetting channels 24.2 are not located on a straight line perpendicular to the second adapter plate 50.2; thus the channels are not guided vertically through the adapter plate 50.2.

This allows the 19 second receiving shafts 52.2 to be arranged marginally as well, adapted to the grid of 96-well microtiter plates 18 with a grid spacing of 9 mm, so that the fitted larger pipette tips 30.2 hit the centre of the microplate wells without any additional offset movement of the pipetting apparatus.

The construction of the second adapter plate 50.2 for the group of larger pipetting channels 24.2 is shown in FIGS. 3D-3H.

Figure 3F:
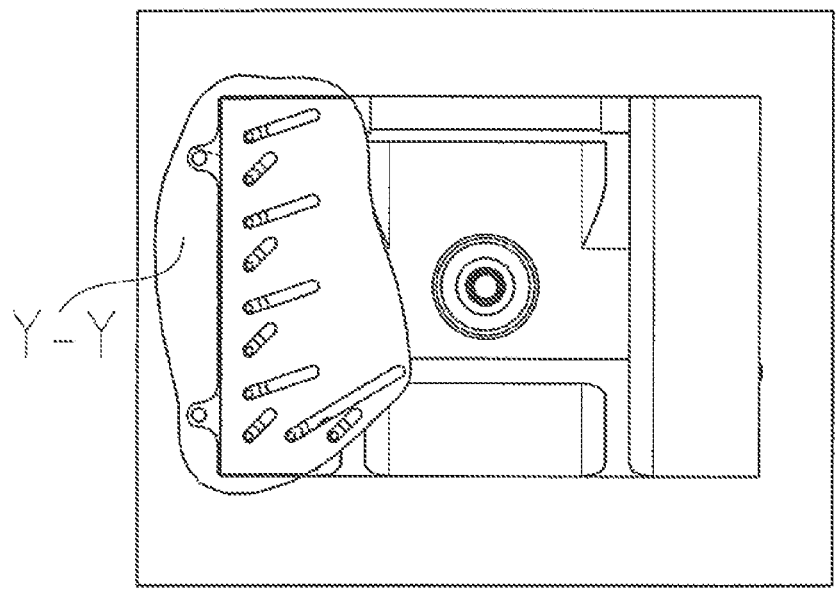
Figure 3G:
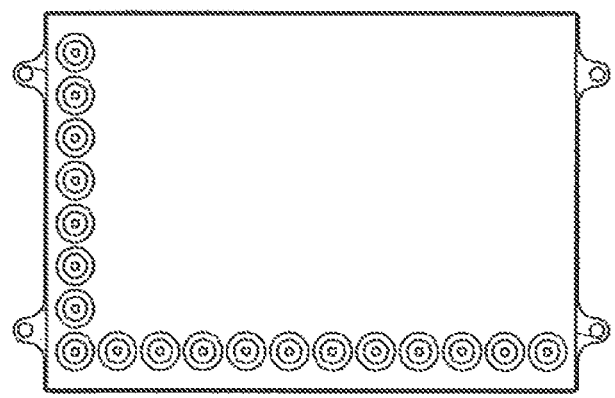

FIG. 3D shows the pipetting apparatus according to the second exemplary embodiment with a second adapter plate 50.2 for the larger pipette tips 30.2, but without the pipette tips 30.2 in a lateral view and in a view from below. Sectional views through various planes of the second adapter 50.2 are shown in FIGS. 3E-3G. A perspective view as well as another sectional view are illustrated in FIG. 3H.

The second adapter plate 50.2 is constituted by three individual plates 53, 54, 55. The course of the channels is clearly illustrated by a channel, in particular with reference to FIG. 3H, section A-A. A channel section, extending vertically into the second adapter plate 50.2 from the channel inlet, is guided through an upper individual plate 53. The channel section terminates in another channel section perpendicular to the former in a central individual plate 54, the width of said other channel section being determined by the thickness of the central individual plate 54, and said other channel section in turn terminating in a channel section which extends vertically out of a lower individual plate 55. As is evident from FIG. 3F, which shows a section through the central individual plate 54, the channel sections have different lengths and different directions. In defining an arrangement pattern for the group of larger pipetting channels 24.2, care must be taken that the channel sections do not intersect in the central individual plate 54 nor form the same air volume. Channel sections which differ in length are accordingly formed with different-sized cross sections. In doing so, care should be taken to provide the channels such that they have a minimal channel volume, so as to form just a small air cushion, if possible.

Figure 3H:
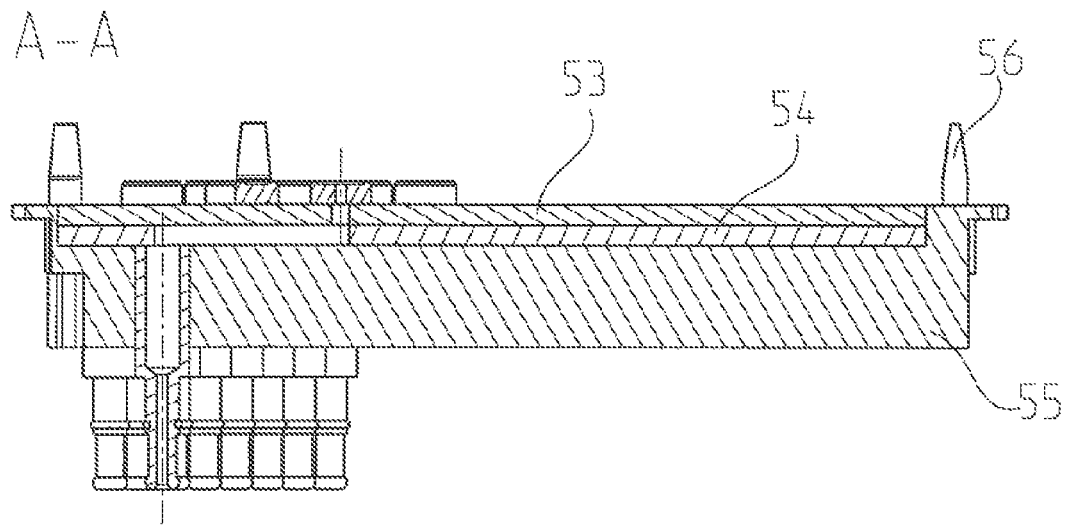
Figure 3H:
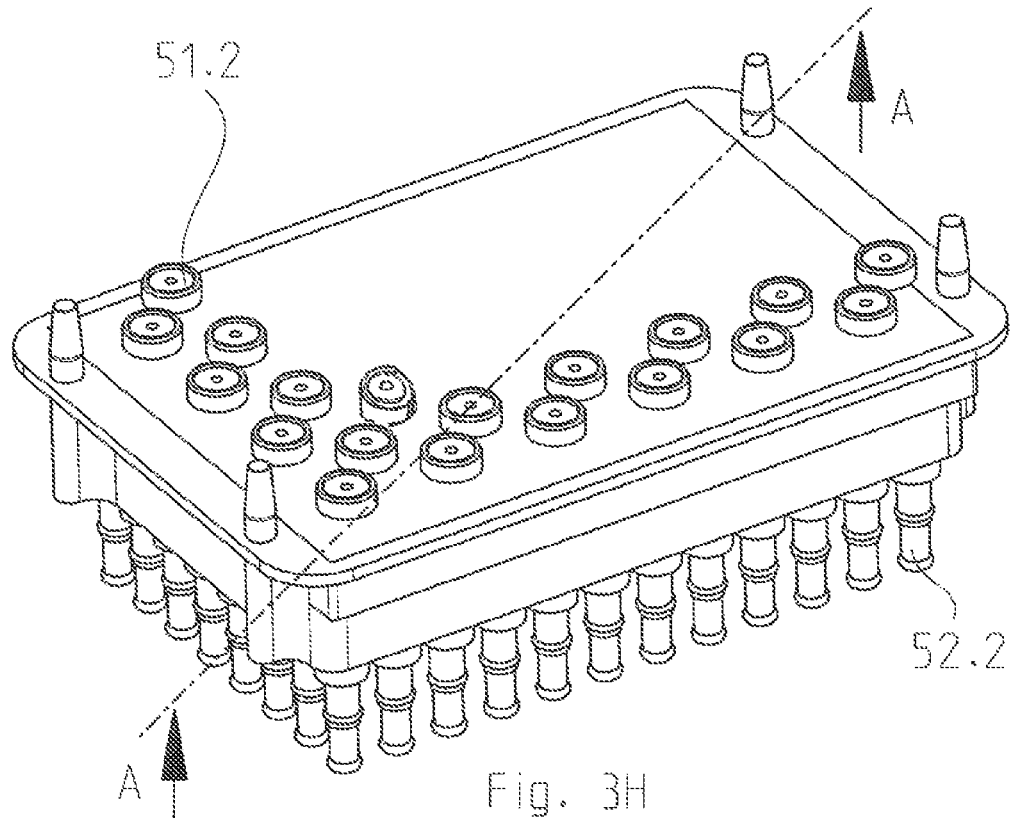

Dowel pins 56, shown for example in FIG. 3H, serve to receive the adapter plate 50.2 automatically, aligned with the pipetting channels 24.1, 24.2, and requiring no adjustment, as described, for instance, in the still unpublished DE 20 2011 000 837.

Further exemplary embodiments of pipetting heads 20, may differ from the two exemplary embodiments described herein, for instance in that further groups of pipetting channels 24.1, 24.2 are present or individual channels are combined in an adapter plate, thereby again increasing the volume which can be handled per pipette tip.

It is possible to combine several smaller pipetting channels 24.1 as well as smaller and larger ones or only several larger pipetting channels 24.2.

Obviously, the described examples of the arrangement pattern for pipetting channels are not bound by whether they were described herein for the larger pipetting channels 24.1 or the smaller pipetting channels, but upon whether they are exchangeable.

The pipetting apparatus described herein adapts the conventional techniques of connecting pipette tips and pipetting channels, namely via a force-fit/form-fit connection to receiving cones or receiving shafts, respectively, or via a force-fit connection only to sealing rings or sealing plates, respectively, and thereby mediates between these two technologies. The exchange of different adapter plates, equipped with different-sized pipette tips, each connected to different-sized pipetting channels, allows the handling of volume ranges previously not achieved. This is made possible because the pipetting channels can be arranged in a grid which does not correspond to the grid of standardized microtiter plates 18 with considerably greater grid spacings, thus allowing much greater differences in the diameter of the pipetting channels.

An advantageous embodiment of a pipetting apparatus with a pipetting head 20 according to the embodiment of FIGS. 3A-3J is made possible by adding an ejection mechanism.

For this purpose, a mechanical system for pipette tip ejection in the form of sheet metal stripper plates is arranged between the adapter plate 50.1, 50.2 and the pipette tips 30.1, 30.2 and encloses the receiving shafts 52.1, 52.2. Most simply, a spring steel sheet with holes is arranged such that it is positioned flat against the adapter plate 50.1, 50.2. The spring steel sheet may be used for tip ejection, for example by two simple mechanical arrangements.

If the pipetting apparatus is moved at least vertically, ejection of the pipette tips 30.1, 30.2 can be effected by means of a simple latch holding back the spring steel sheet. A more elegant way to eject the tips, but one which requires an additional assembly, is to additionally provide a push rod in the pipetting apparatus, which pushes against the spring steel sheet. The push rod in turn may be motor-driven, e.g. by a crank drive or the like. Of course, it is also possible to construct the ejection mechanism in a similar manner as in the applicant's DE 100 22 693, which is incorporated by reference herein.

Another advantageous embodiment of pipetting apparatuses according to the invention is to ensure unambiguous, automatic identification of the magazines, adapters and optionally also the pipette tips, by providing them with identifiers and by including the readout of these identifiers in the device control. There are multiple possibilities to do this, such as:

- mechanical coding of the magazines and adapters in combination with mechanical, electric or optical sensors
- electronic coding by means of a memory chip (ROM—read only memory), for example, which can be read out serially, in combination with an electric contact between the pipetting head and the magazine or adapter
- RFID chip in the adapter/magazine and suitable technology in the pipetting head or the superordinate control system
- Other systems, such as bar code, matrix code, color code, etc.
- In addition or as an alternative, it is also possible, of course, to read features such as shape factors of the pipette tips or other auxiliary identifiers using inexpensive miniature image-processing cameras.

To protect the pipetting channels against soiling as a result of faulty operation, protective filters may be inserted in the receiving shafts. Frequently, different-sized pipette tips are fitted on the same receiving shaft. This has the advantage that smaller volumes can be pipetted/dispensed with better precision and accuracy. The reduction of the so-called dead volume of the entire liquid handling channel contrasts with the risk of overfilling the pipette tip and the resulting contamination of the pipetting channel or its destruction by soiling.

Therefore it is envisaged to integrate a porous protective filter, e.g. made from sintered polyethylene, in each receiving shaft in a replaceable manner. Such protective filters are known as aerosol filters or "aspiration protection" in pipette tips.

While the invention has been particularly shown and described with reference to preferred embodiments thereof, it will be understood by those skilled in the art that various changes in form and details may be made therein without departing from the spirit and scope of the invention.

LIST OF REFERENCE NUMERALS 11 base plate
12 side wall
13 first guide rail
14 second guide rail
15 upper transport vehicle
16 lower transport vehicle
17 holder
18 microtiter plate
20 pipetting head
21 support plate
22.1 smaller-diameter plunger
22.2 larger-diameter plunger
23.1 smaller-diameter cylinder
23.2 larger-diameter cylinder
24.1 smaller-diameter pipetting channel
24.2 larger-diameter pipetting channel
25 sealing plate
30.1 smaller pipette tip
30.2 larger pipette tip
40.1 first magazine
40.2 second magazine
50.1 first adapter plate
50.2 second adapter plate
51.1 first sealing shafts
51.2 second sealing shafts
52.1 first receiving shafts
52.2 second receiving shafts
53 upper individual plate
54 central individual plate
55 lower individual plate
56 dowel pins

What is claimed is:

1. A pipetting apparatus comprising:
a pipetting head including a plurality of pipetting channels disposed in an arrangement pattern, each pipetting channel including a plunger and a cylinder, the plurality of pipetting channels including at least two groups of pipetting channels with different diameters including a group of larger pipetting channels and a group of smaller pipetting channels, each of the at least two groups being disposed in an arrangement pattern in the pipetting head; and
larger pipette tips communicating with the group of larger pipetting channels or smaller pipette tips communicating with the group of smaller pipetting channels;
wherein the at least two groups of pipetting channels comprises exactly two groups of pipetting channels including the group of larger pipetting channels and the group of smaller pipetting channels, the group of larger pipetting channels having a greater diameter and the group of smaller pipetting channels having a smaller diameter, each respective arrangement pattern of the groups of pipetting channels corresponding to an identical grid of a standardized microtiter plate and the arrangement patterns being disposed with a mutual offset.

2. A pipetting apparatus comprising:
a pipetting head including a plurality of pipetting channels disposed in an arrangement pattern, each pipetting channel including a plunger and a cylinder, the plurality of pipetting channels including at least two groups of pipetting channels with different diameters including a group of larger pipetting channels and a group of smaller pipetting channels, each of the at least two groups being disposed in an arrangement pattern in the pipetting head; and
larger pipette tips communicating with the group of larger pipetting channels or smaller pipette tips communicating with the group of smaller pipetting channels;
wherein the at least two groups of pipetting channels comprises exactly two groups of pipetting channels including the group of larger pipetting channels and the group of smaller pipetting channels, the group of larger pipetting channels having a greater diameter and the group of smaller pipetting channels having a smaller diameter, at least one of the respective arrangement patterns corresponding to a part of a grid of a standardized microtiter plate and the arrangement patterns being disposed with a mutual offset.

3. The pipetting apparatus recited in claim 2, wherein the at least one arrangement pattern corresponds to an arrangement of marginal wells of a microtiter plate in a shape of an L.

4. The pipetting apparatus recited in claim 1, wherein a sealing plate contacts the pipetting head, the sealing plate having a pattern of holes including the arrangement patterns of each of the at least two groups of pipetting channels.

5. The pipetting apparatus recited in claim 1, wherein at least one of an at least partially filled, first magazine for smaller pipette tips or an at least partially filled second magazine for larger pipette tips is in force-fitting contact with the pipetting head, the magazines having holes differing in diameter and disposed in hole patterns such that the holes differ in position with respect to an outside edge of the respective magazine.

6. The pipetting apparatus recited in claim 1, further comprising an adapter plate including a number of channels corresponding to the number of larger pipetting channels, the channels of the adapter plate including inlets disposed in a same pattern as the group of larger pipetting channels and outlets disposed in a pattern corresponding to at least a part of a grid of a standardized microtiter plate so as to adapt the pattern of the group of larger pipetting channels to grids of standardized microtiter plates with smaller grid spacings.

7. The pipetting apparatus recited in claim 2, wherein a sealing plate contacts the pipetting head, the sealing plate having a pattern of holes including the arrangement patterns of each of the at least two groups of pipetting channels.

8. The pipetting apparatus recited in claim 2, further comprising an adapter plate including a number of channels corresponding to the number of larger pipetting channels, the channels of the adapter plate including inlets disposed in a same pattern as the group of larger pipetting channels and outlets disposed in a pattern corresponding to at least a part of a grid of a standardized microtiter plate so as to adapt the pattern of the group of larger pipetting channels to grids of standardized microtiter plates with smaller grid spacings.

9. The pipetting apparatus recited in claim 1, wherein the at least one arrangement pattern corresponds to an arrangement of marginal wells of a microtiter plate in a shape of an L.

\* \* \* \* \*